United States Patent [19]
Murray

[11] Patent Number: 5,368,386
[45] Date of Patent: Nov. 29, 1994

[54] MANUAL BONE CEMENT MIXING DEVICE

[76] Inventor: William M. Murray, 2650 Spring Hill La., Enola, Pa. 17025

[21] Appl. No.: 153,218
[22] Filed: Nov. 16, 1993
[51] Int. Cl.⁵ .................................. B01F 13/06
[52] U.S. Cl. .................... 366/139; 366/244; 366/288
[58] Field of Search ............. 366/139, 241, 244, 279, 366/287, 288, 242, 64; 422/99, 225

[56] References Cited

U.S. PATENT DOCUMENTS

| | | | |
|---|---|---|---|
| 795,082 | 7/1905 | Warner . | |
| 2,184,225 | 12/1939 | Moduffee et al. | 259/107 |
| 2,203,135 | 6/1940 | Farrington | 259/102 |
| 2,453,914 | 11/1948 | Hollenback | 259/8 |
| 2,696,022 | 12/1954 | Steinbock et al. | 18/30 |
| 3,131,912 | 5/1964 | Steinbock | 259/108 |
| 3,358,971 | 5/1964 | Steinbock | 259/107 |
| 3,640,510 | 8/1972 | Lea | 259/64 |
| 3,861,656 | 1/1975 | Schmitt | 366/244 |
| 4,079,917 | 3/1978 | Popeil | 366/244 |
| 4,185,072 | 1/1980 | Puderbaugh et al. | 422/99 |
| 4,277,184 | 7/1981 | Solomon | 336/150 |
| 4,721,390 | 1/1988 | Lidgren | 366/139 |
| 4,758,096 | 7/1988 | Gunnarsson | 366/139 |
| 4,787,751 | 11/1988 | Bakels | 366/110 |
| 4,854,716 | 8/1989 | Ziemann et al. | 366/139 |
| 4,961,647 | 10/1990 | Coutts et al. | 366/139 |
| 4,973,168 | 11/1990 | Chan | 336/139 |
| 5,015,101 | 5/1991 | Draenert | 366/349 |
| 5,044,761 | 9/1991 | Yuhki et al. | 366/139 |
| 5,100,241 | 3/1992 | Chan | 366/139 |
| 5,114,240 | 5/1992 | Kindt-Larsen | 366/129 |
| 5,145,250 | 9/1992 | Planck et al. | 366/8 |
| 5,193,907 | 3/1993 | Faccioli et al. | 366/130 |
| 5,252,301 | 10/1993 | Nilson et al. | 422/225 |
| 5,265,956 | 11/1993 | Nelson et al. | 366/139 |

FOREIGN PATENT DOCUMENTS 45-35517  6/1970  Japan .................................. 366/139

OTHER PUBLICATIONS

Depuy, Inc., Flyer "Prism Vacuum Mixing Bowl".
FDA Database Printout Indicating 510K Approval of "Prism Bone Cement Mixing System", on Jan. 5, 1994.
Zimmer Osteobond Vacuum Mixing System, Jun., 1993.
Stryker, High Vacuum Cement Injection System, "Third Generation Cementing Technique", Jan. 1992.
Howmedica, The Simplex Enhancement Mixer, "The Howmedica Experience", Dec., 1985.

*Primary Examiner*—Robert W. Jenkins
*Attorney, Agent, or Firm*—Thomas Hooker

[57] ABSTRACT

A device for mixing bone cement is disclosed. Dry PMMA powder and MMA liquid are mixed in a vacuum chamber by a rotary mixer having a pair of spaced mixing arms. The rotary mixer is manually rotated by a gear drive. The arms of the rotary mixer follow continuous paths, each path having a plurality of loops at the wall of the chamber and curved portions extending across the chamber between loops. The arms move through the cement, break bubbles and thoroughly mix the PMMA and MMA. Gas from broken bubbles is vacuum drawn from the mixer to a vacuum source.

27 Claims, 9 Drawing Sheets

MANUAL BONE CEMENT MIXING DEVICE

FIELD OF THE INVENTION

The invention relates to a device for mixing bone cement.

DESCRIPTION OF THE PRIOR ART

Bone cement is prepared by mixing a very fine cement powder, typically polymethylmethacrylate (PMMA), with a liquid monomer, typically methylmethacrylate (MMA). The cement is used as a grout for implanting prosthetic devices in live bone. Because the cement hardens quickly it is mixed in the operating room and is then transferred directly to a prepared implantation site. The mixing of PMMA and MMA is performed in a housing under sterile conditions. During mixing, gas voids or bubbles are trapped in the viscous cement. These voids form hollow inclusions in the cured cement which weaken the cement and increase the possibility of cement fracture and resultant loosening of an implanted prosthetic device.

Conventional in-bowl and in-syringe bone cement mixing devices have a vacuum mixing chamber, a lid which covers the chamber and seals the PMMA and MMA in the mixing chamber and a rotary mixer which extends through the lid and into the mixing chamber. The mixer is manually rotated to mix the powder and liquid together and form bone cement. It is common practice to connect the mixing device to a vacuum source to reduce the internal pressure in the mixing device in an attempt to remove bubble gas from the cement during mixing.

Bone cement is mixed by placing fine PMMA powder and MMA liquid in a mixing chamber, either the bowl of an in-bowl mixer or the barrel of a syringe cartridge which is in turn placed in a housing. The mixing device is closed with a mixer extending into the cement powder and liquid and the device is connected to a vacuum source. The mixer is manually operated for a measured time interval to mix the powder and liquid and form the bone cement.

When the mixing device is closed, the vacuum source very rapidly reduces the pressure within the closed mixing chamber and rapidly draws the relatively large volume of air between the very fine dry particles of powdered PMMA out of the mixing chamber holding the PMMA. This occurs before the powder is fully wetted by the MMA and captured in a liquid or partially liquid body of cement.

The pressure within the chamber is often reduced sufficiently rapidly to draw the air in the PMMA powder out of the powder explosively. Fine PMMA particles are entrained with the air and are drawn up from the bottom of the chamber, much like a geyser. The explosive extraction of air from between the particles of PMMA is undesirable because it may remove sufficient PMMA from the mixing chamber to change the composition of the bone cement and may coat the upper walls of the mixing device with powdered PMMA. PMMA powder may also be drawn into the vacuum line.

Rotation of the mixer in a conventional bone cement mixing device mixes the powdered PMMA and liquid MMA together to form a body of bone cement. During this mixing remaining air in the PMMA powder forms bubbles in the cement. Shallow bubbles located near the top of the cement tend to rise to the surface and break. Deep bubbles do not rise to the top of the viscous cement. As the mixer is moved through the cement it contacts bubbles in its swept path. These bubbles are broken by the mixer and withdrawn from the chamber. However, the mixer does not slice or break all of the bubbles in the cement. The path swept by a conventional mixer does not move the mixer through or sufficiently near all the bone cement in the mixing chamber to break all bubbles and release all bubble gas.

Bubbles deep in the liquid cement which are not sliced by the mixer are not removed from the cement. The viscosity of the cement prevents these bubbles from rising to the top of the cement and breaking. The bubbles in the fully mixed cement remain in the cement as the cement is removed from the mixing chamber and placed in an implantation site. The bubbles form hollow inclusions in the hardened cement. Joints formed by conventionally mixed bone cement are weakened by the inclusions.

SUMMARY OF THE INVENTION

The invention is a device for uniformly mixing bone cement powder and liquid to make a body of bone cement of the proper consistency having a reduced number of gas bubbles. Powder geysers are eliminated. The arms of a rotary mixer are moved through a mixing chamber sufficiently close to each volume of cement in the chamber to thoroughly mix all of the cement to the proper consistency and break substantially all bubbles in the cement. Bubble gas is drawn from the mixing chamber by vacuum.

Two embodiments of the mixing device are disclosed. Each embodiment mixer device includes a mixer housing defining a mixing chamber, a cap closing the top of the mixer housing and supporting a manually operated mixer drive, a rotary mixer attached to the cap and rotated by the drive and a vacuum tube fitting. The two embodiments use different drives for rotating the mixer in the chamber.

In the first embodiment, the drive includes a three gear train which simultaneously rotates the opposed arms of the rotary mixer extending into the PMMA and MMA about the axis of the mixer and moves the mixer in a circle around the axis of the chamber. Each arm is moved along a continuous path having loops sweeping close past the sidewall of the chamber and portions extending through the center of the chamber. The paths of the two arms through the cement are angularly offset to assure that the arms sweep through or very close to all of the cement in the chamber, mix the cement thoroughly and uniformly, and break substantially all bubbles to permit vacuum withdrawal of released bubble gas. The mixed cement body has a proper consistency and contains reduced bubbles. Movement of the arms past the chamber sidewall wipes adhered powdered cement from the arms and the sidewall for improved mixing.

The second embodiment mixing device uses a two gear drive which moves the mixer arms along paths like the paths of the mixer arms in the first embodiment to assure that the arms sweep through or very close to all of the cement in the chamber, mix the cement thoroughly and uniformly and break substantially all bubbles to permit vacuum withdrawal of released bubble gas.

Each of the two mixing devices may be used with automatic shutdown vacuum source. The source is connected to mixing device by vacuum tube and includes a vacuum pump which reduces the pressure within the mixing chamber during mixing in order to withdraw bubble gas from the bone cement. After mixing has been completed, the vacuum tube is removed from the mixing device, the cap is removed and the mixed cement is flowed to an application site.

The vacuum source senses the increase in pressure in the vacuum tube when the tube is disconnected from the mixing device and automatically shuts down the vacuum pump in order to prevent vacuum drawing of contaminants into the vacuum tube. Shutdown is automatic and does not require the attention and time of operating room personnel.

Other objects and features of the invention will become apparent as the description proceeds, especially when taken in conjunction with the accompanying drawings illustrating the invention, of which there are nine sheets and two embodiments.

DESCRIPTION OF THE PREFERRED EMBODIMENTS

First embodiment mixing device 10 shown in FIGS. 1–4 is used to mix bone cement powder and a liquid under vacuum to make a body of uniformly mixed bone cement having reduced bubbles. The bone cement powder is typically polymethylmethacrylate (PMMA) and the liquid mixed with the powder is typically a liquid monomer methylmethacrylate (MMA). Powder geysers are eliminated.

Figure 1:
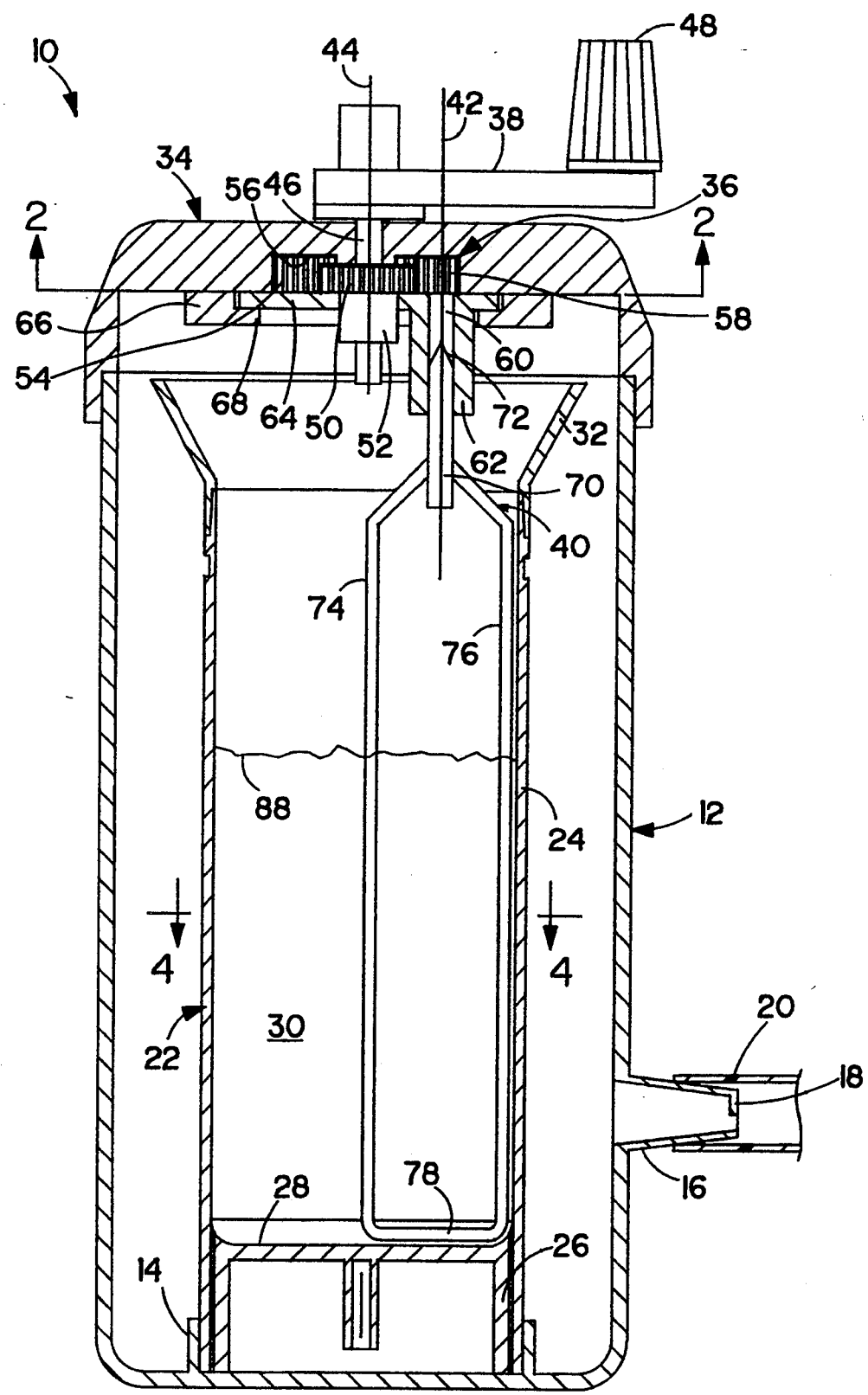
FIG. 1 is a vertical sectional view taken through a first embodiment bone cement mixing device.
Figure 2:
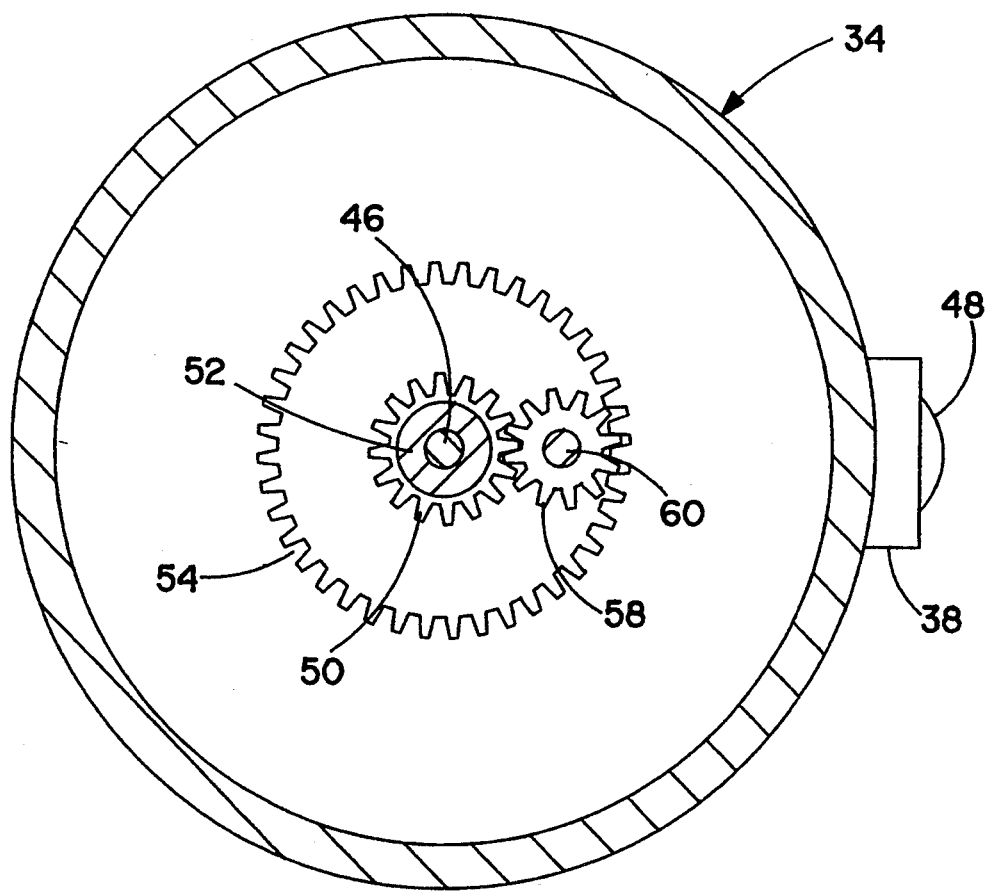
FIG. 2 is a sectional view taken along line 2—2 of FIG. 1.
Figure 3:
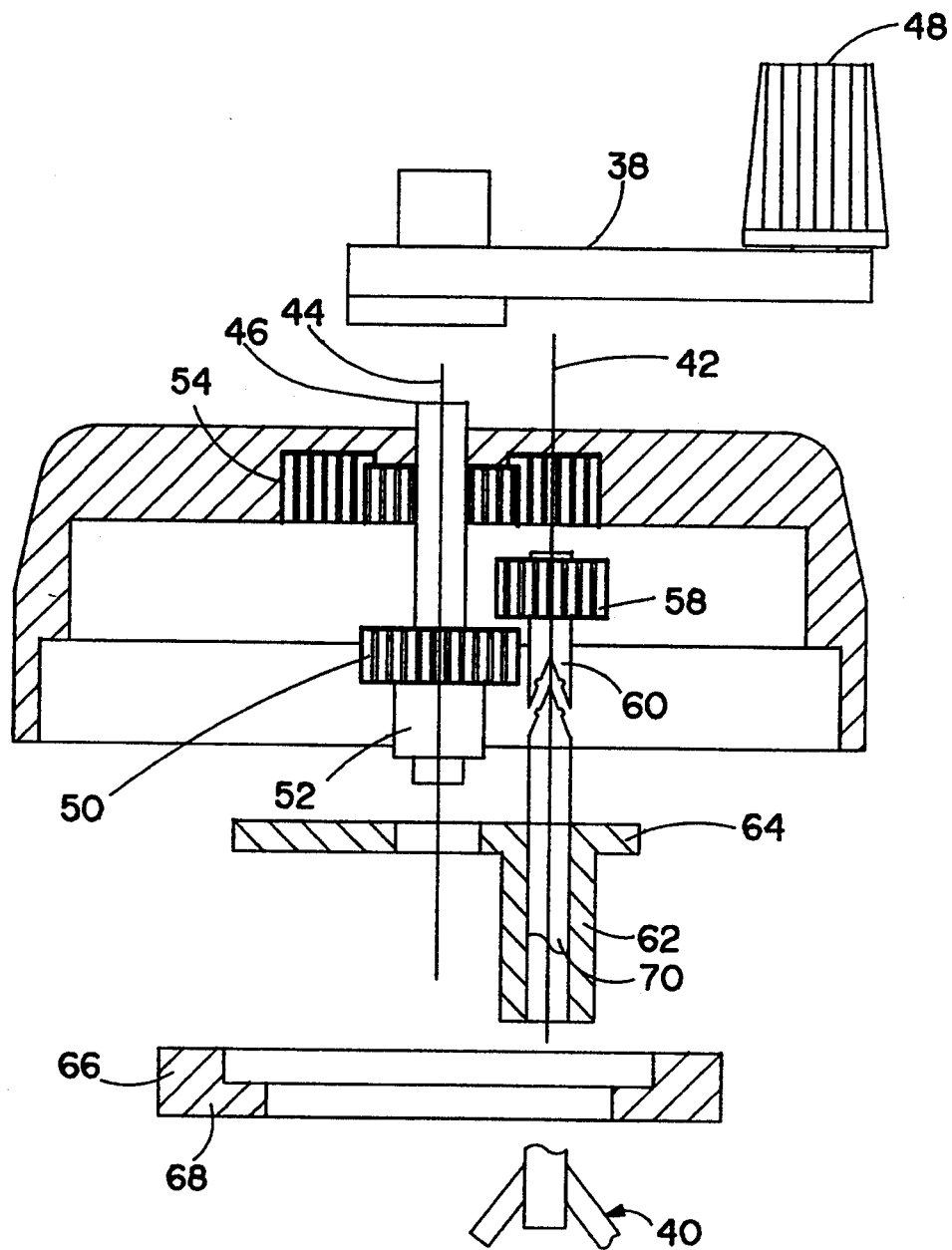
FIG. 3 is an enlarged exploded view illustrating the components of the drive of the mixer shown in FIG. 1.

Mixing device 10 includes a hollow housing 12 having an open top, a cylindrical sidewall and a closed bottom wall with an integral cartridge socket 14 projecting up from the bottom wall. The housing also includes integral vacuum tube attachment fitting 16 located on the sidewall near the closed bottom. The fitting defines a passage extending through the housing sidewall. A restriction 18 in the fitting limits the outward flow of air through the fitting. As shown in FIG. 1, one end of flexible vacuum tube 20 is connected to fitting 16. The other end of the tube is attached to a conventional vacuum source or to specialized vacuum source 110 shown in FIG. 9. The restriction 18 prevents a very sudden reduction of pressure within the housing when the housing is first connected to a vacuum source without limiting pressure reduction within the housing. The pressure in the housing is reduced sufficiently slowly to prevent powder PMMA geysers. During mixing, the pressure in the device is reduced to the pressure of the source to withdraw released bubble gas.

It should be noted that the rate of outflow of air from the interior of the housing may be suitably reduced by placing an airflow restriction, like restriction 18, anywhere in the path of flow and through the vacuum source. With most types of vacuum pumps, the restriction may even be placed on the pump's outflow side. A number of restriction, located at different points along the path of air flow, may be used to provide the total amount of restrictions which is required. Plural restrictions can facilitate reduction of initial flow of air from the mixing device to compensate for the properties of the particular operating room vacuum system, including the length and interior diameter of the vacuum tube, the vacuum achievable by the vacuum pump and the rate at which the pump exhausts air from the mixing device.

A hollow cylindrical syringe cartridge 22 having opposed open and closed ends, a cylindrical sidewall 24 and a diameter smaller than the diameter of housing 12 is fitted within the housing with the lower end of the cartridge seated in socket 14. Piston 26 closes the lower end of the cartridge. The piston has a flat upwardly facing mixing face 28. The sidewall 24 and the mixing face 28 define cement mixing chamber 30. Filling funnel 32 is removably mounted on the upper open end of cartridge 22 to facilitate pouring PMMA powder and liquid MMA into the mixing chamber. The funnel is removed after mixing has been completed and before the cartridge is loaded in an applicator gun for flowing the mixed bone cement to an application site.

Cap 34 is fitted on the open upper end of housing 12 and serves to close the interior of the housing. The cap supports a manually operated three gear mixer drive 36. Crank arm 38 on the top of the cap actuates the drive to rotate mixer 40 about mixer axis 42 and simultaneously move the mixer in a circle around central chamber axis 44. The housing and cap may be made from plastic or other suitable material.

Three gear drive 36 includes an input drive shaft 46 located on chamber axis 44 and extending through the thickness of cap 34 with ends above and below the cap. Crank arm 38 is attached to the upper end of shaft 46 and carries a knob 48 extending upwardly from the outer end of the crank arm to permit manual rotation of the shaft. The drive 36 also includes an input gear 50 and hub 52 located on the lower end of shaft 46 inside the cap. An interior gear 54 is formed on the circumference of recess 56 in cap 34 and surrounds and is concentric with the chamber axis 44 and input gear 50 which is also located in the recess. Mixer gear 58 is located in the recess between the input gear and the interior gear and includes teeth engaging the teeth of the input gear and the teeth of the interior gear. The mixer gear 58 is mounted on a short rotary output shaft 60 which extends into the bore of a mounting bushing 62 on circular plate 64. The output shaft extends about halfway through the bore. The plate covers the recess 56 and is held against lower surface of cap 34 by a retainer collar 66 which has an inwardly facing lip 68 extending under the circumferential edge of plate 64. The collar permits rotation of the plate around the chamber axis 44 as the gear 50 is rotated by crank arm 38. The plate rotates on the lip. Hub 52 on gear 50 extends through a central opening in plate 64 to permit relative rotation of the plate and gear.

Rotary mixer 40 is removably attached to shaft 60. The mixer includes a short central shaft 70 having an upper end 72. End 72 is extended into the bore of bushing 62 and removably attached to the lower end of output shaft 60 so that rotation and movement of mixer gear 58 rotates and moves the mixer. The connection between shafts 60 and 70 is of conventional design and permits ready attachment and removal of mixers so that device 10 may be used to mix a number of batches of cement.

The mixer 40 includes a pair of vertical mixing arms 74 and 76 each extending parallel to central shaft 70 along the length of the mixing chamber 30 in cartridge 22 and spaced an equal distance to either side of the shaft. The upper ends of arms 74 and 76 are joined to the central shaft at the top of the chamber. The lower ends of the arms are joined by cross arm 78. The arm 78 is located immediately above the mixing surface 28 of piston 26. The corner between the lower ends of vertical arms 74, 76 and the cross arm closely conforms to the radius at the lip of the piston 26.

Figure 4:
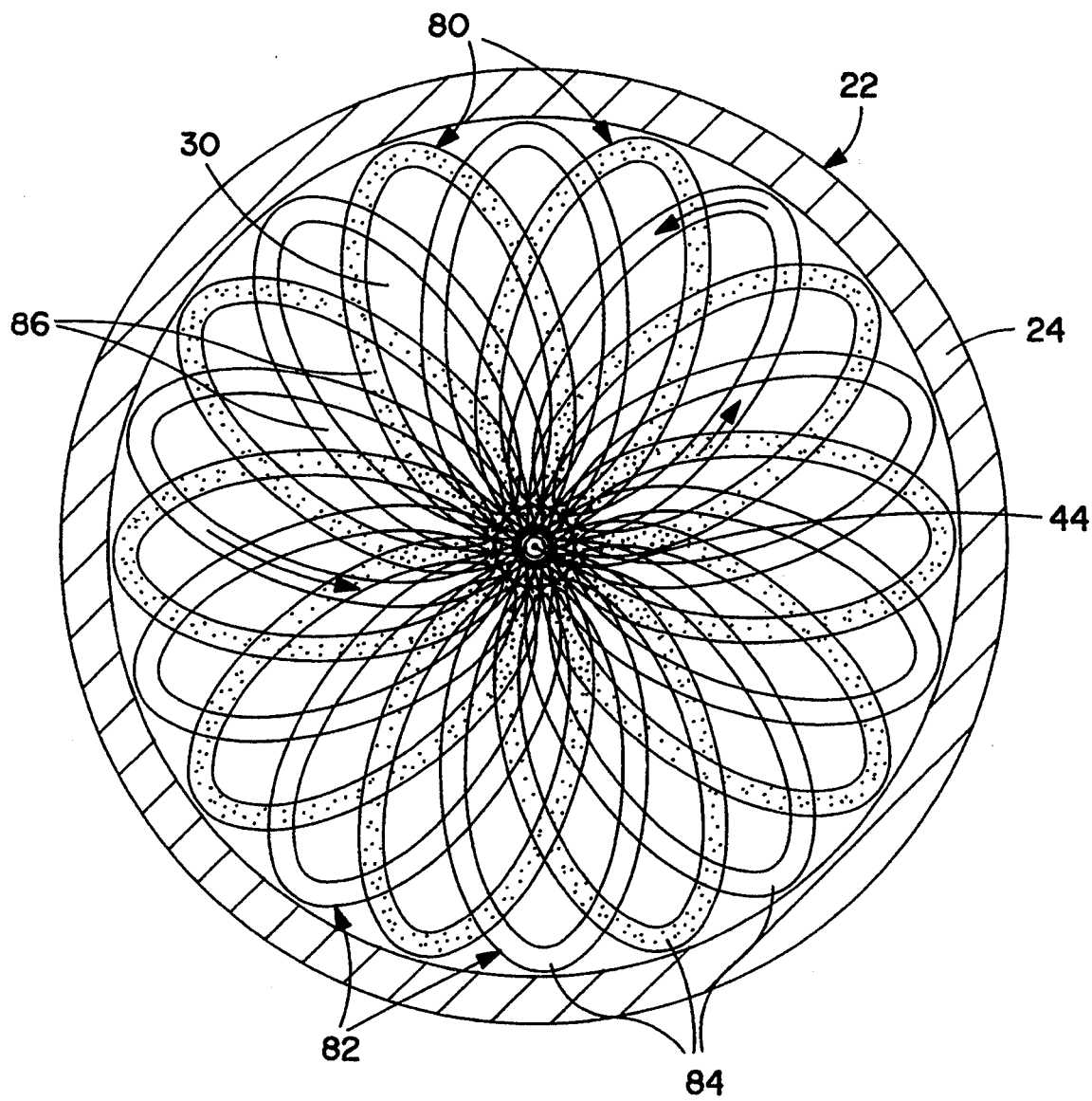
FIG. 4 is a sectional view taken along line 4—4 of FIG. 1 illustrating the mixing paths swept by the mixer.

Arms 74 and 76 are equally spaced on opposite sides of central shaft 70 and are spaced apart from each other a distance slightly less than the radius of the interior of the mixing chamber 30. Each arm is spaced from mixer axis 42 a distance approximately equal to one quarter of the diameter of the mixing chamber. In this way, as shown in FIGS. 1 and 4, rotation of the mixer about axis 42 and movement or translation of the mixer axis 42 around axis 44 moves each vertical arm 74, 76 through a continuous path 80, 82. In FIG. 4, path 80 is shown stippled in order to distinguish the path visually from path 82. In each path the arms are swept through a number of loops 84 spaced around the circumference of the chamber sidewall 24 very close to the sidewall, and are moved along smooth curved sections or portions 86 extending between successive loops 84 along the path and passing through the chamber axis 44.

Operation of the mixing device 10 will now be described.

Syringe cartridge 22 is placed in the empty housing 12 with the piston end of the cartridge seated in socket 14. A filling funnel 32 is placed on the open end of the syringe cartridge as shown. The required amounts of dry PMMA powder and MMA liquid are poured into mixing chamber 30. The combined volume of the PMMA and MMA may fill the chamber to level 88, although greater or smaller volumes of bone cement may be mixed as required. See FIG. 1.

After the PMMA and MMA are placed in the chamber, the cap 34 with attached rotary mixer 40 is placed on the open end of the housing with mixer 40 extended down into the mixing chamber and the PMMA and MMA mixture and cross arm 78 immediately above mixing surface 28 as shown in FIG. 1. The cap seals the PMMA, MMA and trapped air in housing 12. With the vacuum source operating, vacuum tube 20 is connected to fitting 16 to connect the interior of the mixer to the vacuum source. Mixing is started by turning crank 38.

When vacuum tube 20 is attached to fitting 16 restriction 18 prevents very rapid reduction of the pressure in the interior of the housing during initial mixing and wetting of the PMMA powder in chamber 30. In this way, the pressure within the chamber is slowly reduced to the pressure of the vacuum source for efficient removal of air from between particles of dry PMMA without forming explosions or geysers of PMMA powder. Air trapped in the mixture, including bubble gas, is vacuum withdrawn without entraining dry cement particles. After initial mixing of the cement, the pressure in the chamber is lowered to the pressure of the vacuum source.

The PMMA and MMA are mixed for a period of about 90 to 120 seconds. During the mixing cycle, crank 38 is rotated in one direction to rotate shaft 46 and gear 50 in the same direction. Rotation of the crank and input gear 50 rolls the mixer gear 58 around the interior gear 54 in a direction of rotation about axis 42 opposite to the direction of rotation of the crank around axis 44. The mixer is moved in a circle around axis 44 at a slower speed than the crank because there are a greater number of teeth on the interior gear than on the input gear.

During mixing, the mixer moves or translates in a circle around chamber axis 44, the mixer rotates about axis 42 and the vertical mixer arms 74 and 76 follow the continuous paths 80 and 82 shown in FIG. 4. By using the gear ratios shown, each continuous path includes ten like loops 84 which are spaced around the circumference of chamber 30 and joined by smooth curved sections 86 passing through chamber axis 44. During each 360 degree rotation of mixer 40 about mixer axis 42 each mixing arm 74 and 76 is moved from the end of one loop along a curved section 84 to the next successive loop. The individual adjacent loops swept by the two mixer arms are offset by 18 degrees. See FIG. 4. The rotary mixer is rotated three times around axis 44 in order to move the mixer arms along the complete lengths of paths 80 and 82.

Rotation of the crank during mixing moves the arms throughout the chamber sufficiently close to all of the cement in the chamber to thoroughly mix the bone cement components and slice through substantially all of the gas bubbles trapped in the cement. The liquid cement flows in the chamber during mixing to further assure the cement is thoroughly mixed and bubbles are sliced. Released bubble gas is drawn away by vacuum. Mixing is enhanced by sweeping arms 74 and 76 close past the sidewall of chamber 30 as they move through loops 84. As the arms move past the sidewall, cement and liquid adhered to the arms and to the sidewall are mixed with the body of cement in chamber 30. Cement and liquid adhered to the mixing face 28 and cross arm are likewise mixed with the cement in the chamber.

As the mixing arms are moved around paths 80 and 82, the arms slice through bubbles in the mixture and break bubbles. It is believed that the arms displace the viscous mixture to either side of the arms and create voids or spaces directly behind the arms with each void extending vertically to and through the surface of the cement body at level 88. The arms extend from the bottom of the chamber up to and past the top of the body of cement in the chamber. Gas from bubbles broken by the arms is believed to flow up the voids and is vacuum-drawn from the mixing device. Shallow bubbles tend to rise through the cement to the surface 88 and break. During mixing, the cement flows in the chamber so that substantially all deep bubbles are broken by the arms and the freed bubble gas is vacuum withdrawn.

At the completion of the mixing cycle, the vacuum in the chamber is released by removing tube 20 from fitting 16, the cap is removed from the housing and the rotary mixer is withdrawn from the mixing chamber.

The syringe cartridge containing the body of freshly mixed bone cement is removed from the housing socket, the funnel is removed and the cartridge is placed in a bone cement applicator. The well mixed and essentially bubble-free bone cement is then flowed to a prepared implant site and the mounting stem of a prosthetic device is extended into the cement. The cement rapidly hardens to form a strong joint securing the prosthetic element in place. The joint is substantially free of gas inclusions.

As indicated, the mixer 40 is removably connected to shaft 60. After mixing and opening of the housing, the mixer 40 is detached from shaft 60 and discarded. A new mixer may be inserted into bushing 62 to engage shaft 60 and prepare device 10 for mixing another batch of bone cement.

Figure 5:
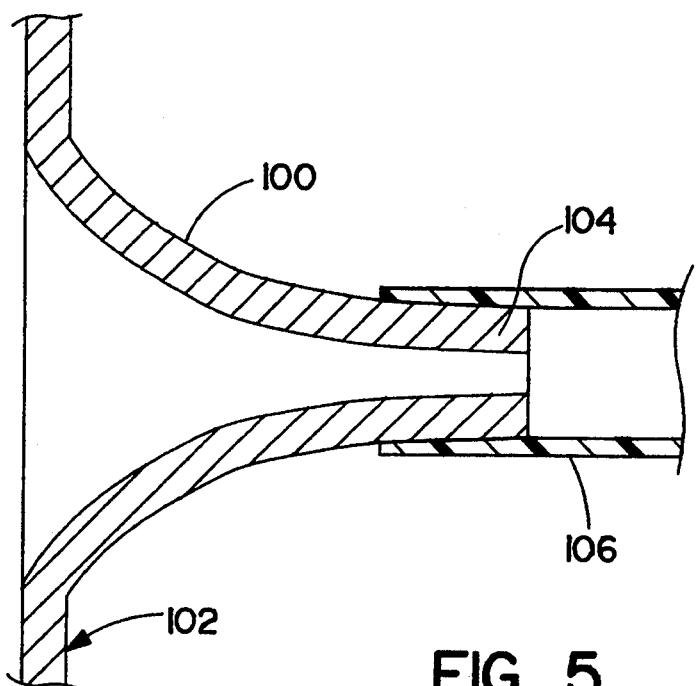
FIG. 5 is a view of an alternative embodiment vacuum port for the mixer.

FIG. 5 illustrates a second embodiment vacuum tube attachment fitting 100 formed in the wall of a housing 102 like housing 12 of mixing device 10. The fitting 100 is similar to fitting 16 but has a concave exterior shape and a small diameter tube mounting end 104 facing outwardly from the housing. One end of small diameter vacuum tube 106 is fitted on end 104. The other end of the tube is attached to a vacuum source. This tube may be of a diameter approximately equal to the diameter of tubing which is used conventionally for flowing intravenous fluids and is appreciably smaller in diameter than the diameter of conventional vacuum tubing 20. The diameter of conventional vacuum tubing is approximately 0.375 inch while the interior diameter of the small vacuum tube is less than 0.1 inch. The interior diameter selected may be made sufficiently small to form a restriction which reduces the outward flow of air from the interior of the housing during initial mixing to a rate insufficient to lift or draw dry PMMA powder up from the mixing chamber 30. Air flowed through tube 106 reduces the pressure in the housing to aid in removal of bubble gas.

Figure 9:
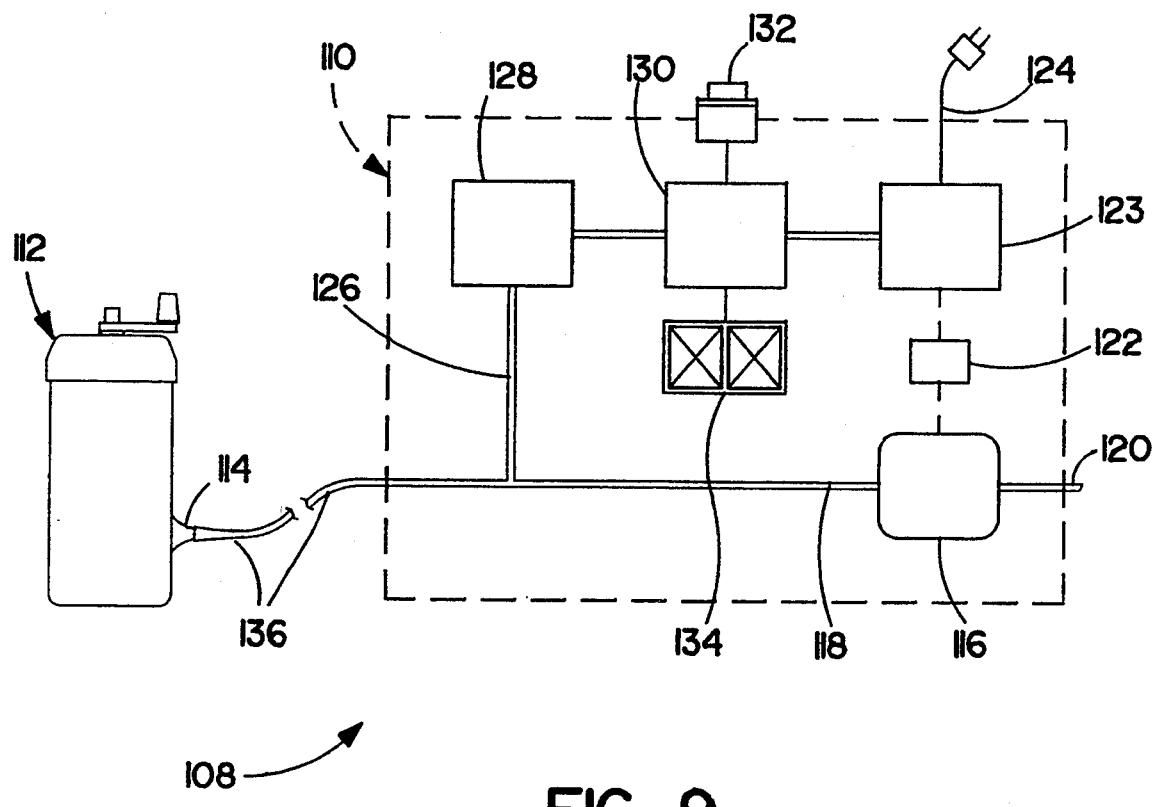
FIG. 9 illustrates a bone cement mixer and an automatic shutdown vacuum source.

Different types of vacuum sources may be used to withdraw air from device 10 during bone cement mixing. These vacuum sources include the operating room vacuum system, a manually actuated dedicated pump operated by compressed gas or electricity, or an automatic shutdown vacuum source as shown in FIG. 9.

Figure 10:
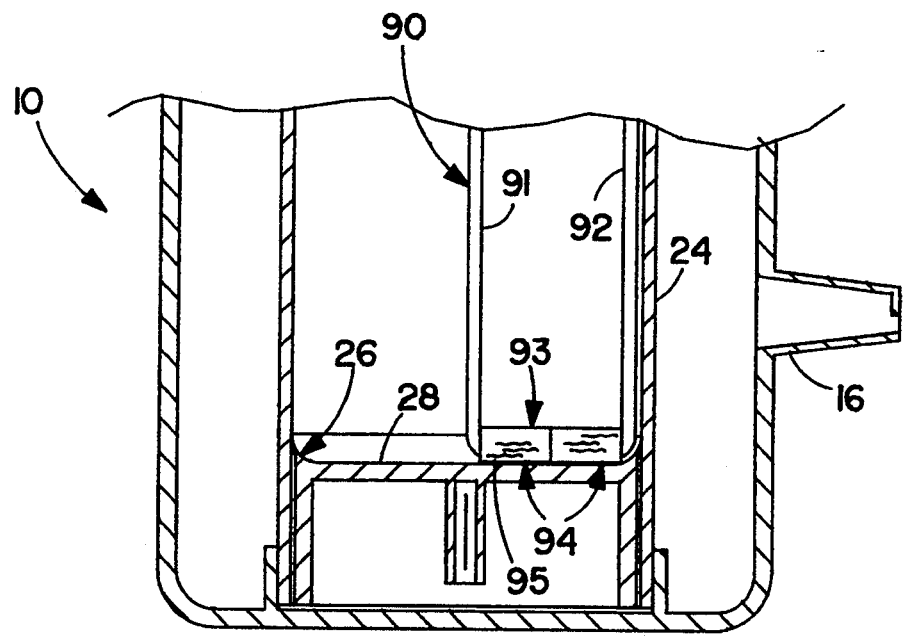
FIG. 10 is a sectional view illustrating the lower end of a second embodiment cement mixer in the mixing device of FIG. 1.
Figure 11:
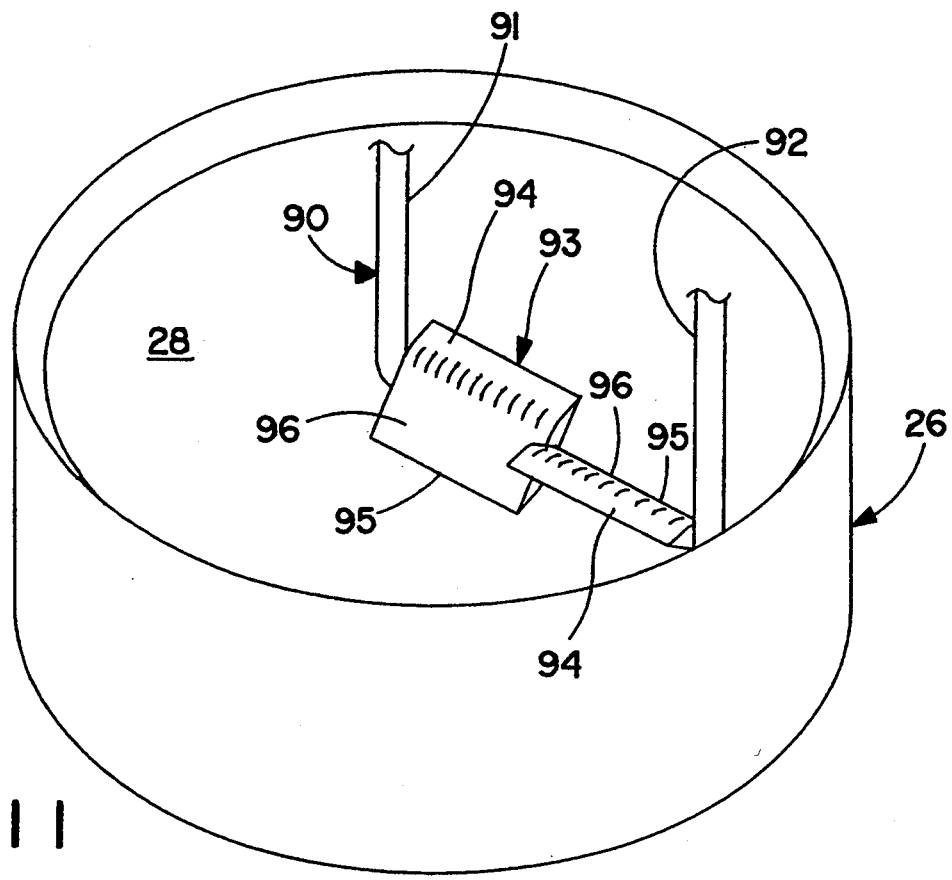
FIG. 11 is an isometric view of the piston and lower end of the mixer of FIG. 10.

FIGS. 10 and 11 illustrate a second embodiment mixer 90 similar to mixer 40 in mixing device 10. Mixer 90 includes a central shaft like shaft 70 and a pair of spaced parallel mixing arms 91 and 92 like arms 74 and 76. Cross arm 93 joins the lower ends of the mixing arms 91 and 92. The mixer 90 is removably attached to shaft 60 like mixer 40.

The cross arm 93 includes a pair of angled mixing blades 94 joined at the center of the arm. Each blade extends from the center of the cross arm to the lower end of one of the mixing arms 91, 92. As shown in FIG. 11, each blade includes a lead edge 95 located immediately above the mixing face 28 of piston 26 and a deflector 96 sloping upwardly and rearwardly of the lead edge. The lead edges 95 of the two blades 94 face in opposite directions.

During bone cement mixing, mixer 90 is rotated in a direction to rotate the leading edges around the mixing face 28 so that the powdered cement, liquid and cement mixture on the face of the piston are scraped from the face and deflected upwardly into the main body of cement in the mixing chamber and are thoroughly mixed with the body of cement. The mixture in the main body of cement in the chamber is also drawn down into the spaces behind the blades during rotation of the mixer to further enhance mixing. In this way, mixer 90 positively scrapes the cement constituents from the top of the piston and mixes them with the body of liquid cement in the mixing chamber. During mixing arms 91 and 92 follow paths like paths 80 and 82 to thoroughly mix the cement and break bubbles. Released bubble gas is withdrawn as previously described.

Suitable indicia such as an arrow may be affixed to the top of cap 34 or on the handle to indicate the proper direction of rotation of handle 38 required to rotate mixer 90 so that the lead edges of the mixing blades are moved forward around the top of the piston and scrape material from the piston. Mixers 40 and 90 may be made from metal or molded plastic.

Figure 6:
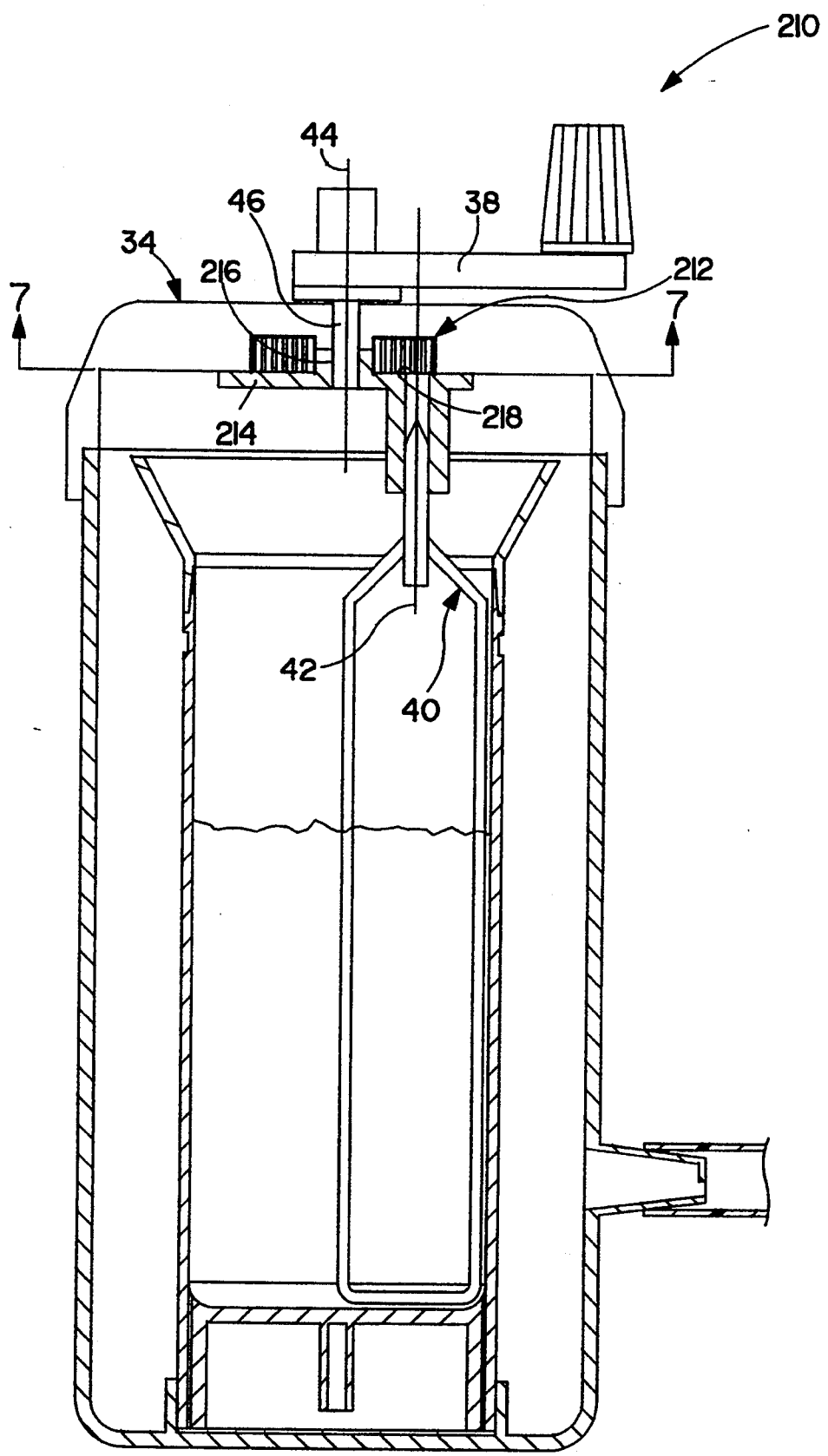
FIG. 6 is a vertical sectional view taken through a second embodiment bone cement mixing device.
Figure 7:
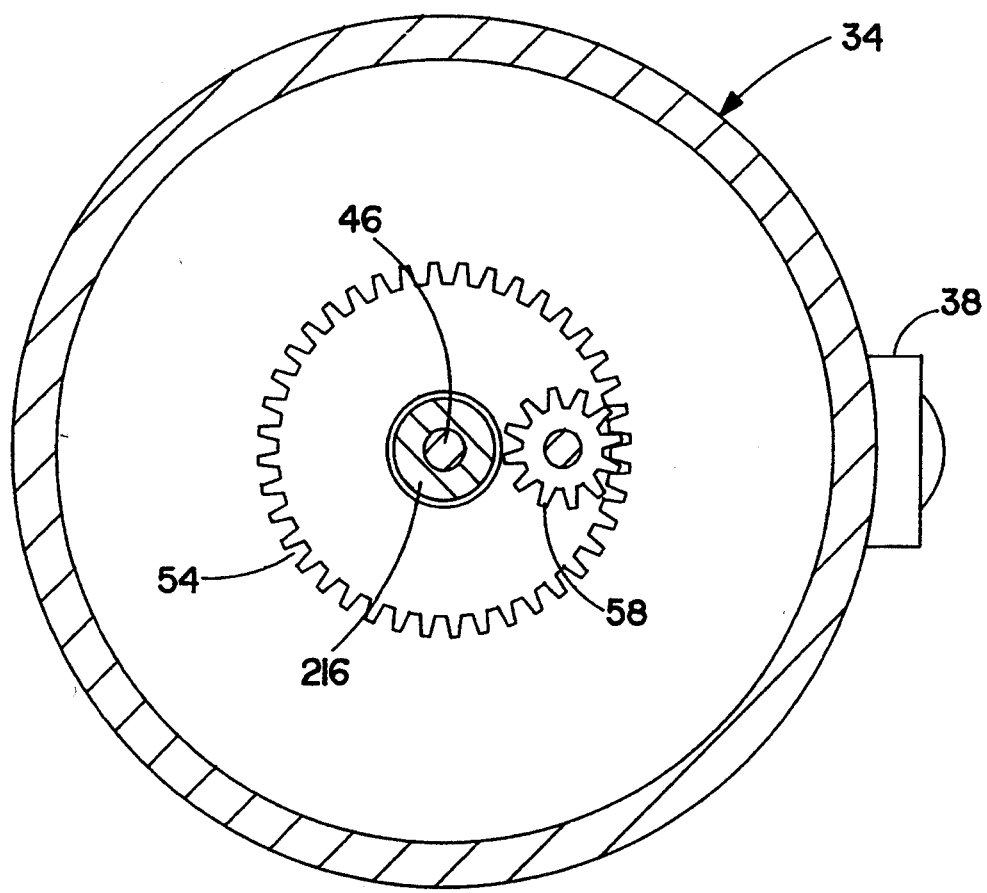
FIG. 7 is a sectional view taken along line 7—7 of FIG. 6.
Figure 8:
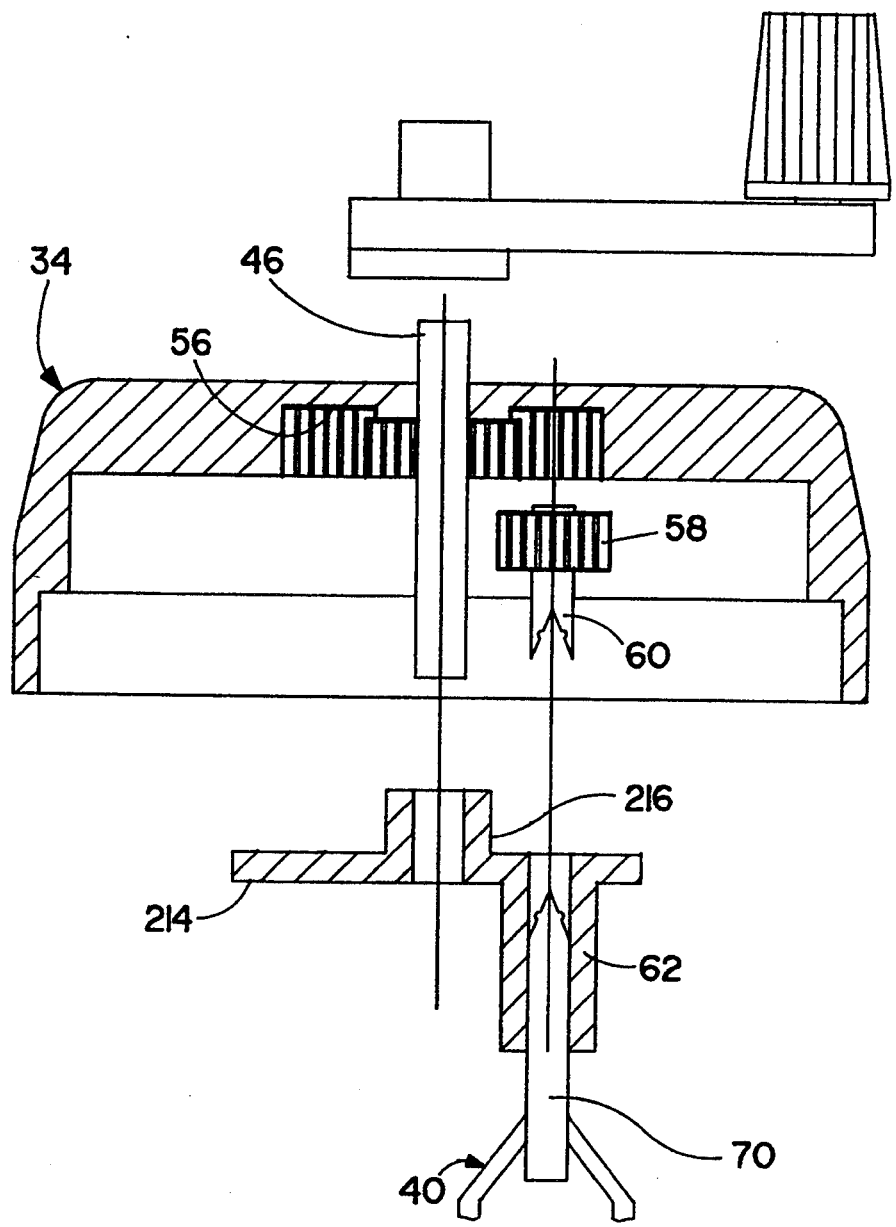
FIG. 8 is an enlarged exploded view illustrating the components of the drive of the mixer shown in FIG. 6.

A second embodiment mixing device 210 is shown in FIGS. 6–8. The second embodiment mixing device is similar to the first embodiment mixing device 10 but uses a manually operated two gear mixer drive 212.

Cap 34 supports drive 212. Crank arm 38 actuates the drive to simultaneously rotate and move the mixer 40 in the same manner and around the same paths 80 and 82 as previously described. Drive 212 includes input drive shaft 46 located on chamber axis 44 and extending through cap 34 and circular plate 214. Crank 38 is attached to the upper end of the shaft. Circular plate 214 is similar to circular plate 64 except that hub 216 surrounds and is connected to shaft 46. The shaft holds the plate against the interior surface of the cap. The plate covers recess 56 in cap 34. Hub 216 of plate 214 is located within recess 56 with the top of the hub in contact with the upper surface of the recess. See FIG. 6.

Drive 212 also includes mixer gear 58 and interior gear 54 which is formed on the circumference of recess 56. The teeth of mixer gear 56 are engaged with the teeth of the interior gear. The mixer gear is mounted on short rotary output shaft 60 which extends into hub 62 and is removably connected to shaft 70 to rotate mixer 40.

The housing 18 of mixing device 210 may include either a first embodiment vacuum hose attachment fitting 16 shown in FIG. 6 or a second embodiment vacuum hose attachment fitting 100 shown in FIG. 5.

Operation of mixing device 210 will now be described.

After the required amounts of PMMA and MMA are placed in chamber 30, the cap 34 supporting drive 212 and mixer 40 is placed on the top of housing 18 sealing the contents of the housing with the mixer extending into the PMMA and MMA mixture. Vacuum tube 20 is then connected to fitting 16.

The PMMA and MMA are mixed by rotating crank 38 clockwise. As the crank is rotated clockwise, shaft 46 and plate 214 also rotate clockwise. The mixer gear 58 is moved clockwise around axis 44 and is rotated about axis 42 in a counterclockwise direction. Arms 74 and 76 follow the continuous paths 80 and 82 shown in FIG. 4 and gas is withdrawn from the mixture in the manner previously described. After mixing is completed, the tube is disconnected from the fitting. The cap is opened and the cement is flowed to an application site as described.

FIG. 9 illustrates a system 108 for mixing bone cement. The system includes an automatic shutdown vacuum source 110, a bone cement mixing device 112 and a vacuum tube 136 joining the source and device. Device 112 may be identical to either device 10 or device 210 and includes a vacuum tube attachment fitting 114 like either fitting 16 or 100.

The automatic shutdown vacuum source 110 includes a vacuum pump 116, a low pressure inlet line 118 connected to the pump inlet port and a high pressure discharge port 120. The pump 116 is powered by electric motor 122 which is connected to a source of electricity through power line 124. The vacuum line 126 connects the inlet line 118 to an electronic pressure transducer 128 which in turn is electrically connected to shutdown control circuit 130. A manually activated start switch is connected to circuit 130. Power switch 123 in line 124 is controlled by circuit 130. The control circuit 130 is of conventional design. The electronic pressure transducer 128 may be of the type manufactured by Motorola, Inc. of Schaumburg, Illinois.

Power switch 123 is normally open. Actuation of momentary-type start-up switch 132 closes the switch 123. The control circuit 130 opens the switch 123 to turn motor 122 off when a sudden increase in pressure in line 126 is sensed by transducer 128. A vacuum indicator 134, controlled by circuit 130, provides a visual indication of the level of vacuum in the interior of device 112 during cement mixing. The indicator 134 may have an analog or digital read out.

Bone cement is mixed in the operating room. Mixer 112 is maintained in a sterile field during mixing. Cement is mixed using vacuum source 110 by placing a syringe cartridge in an empty housing, and attaching one end of sterile vacuum tube 136 to fitting 114. The other end of the tube is connected to the inlet of line 118. At this time, the pump is not in operation. The PMMA and MMA to be mixed are placed in the mixing chamber. The cap is then attached to the top of the housing with the mixer extending into the mixing chamber. An assistant actuates switch 132 to supply power to control circuit 130, close switch 123 and actuate motor 122 and the vacuum pump 116. The vacuum pump withdraws air from the mixer without forming powder geysers. The cement is mixed and bubble gas is removed, as previously described. During mixing, the attendant monitors indicator 134 to assure that the pressure within the mixer has been properly reduced for efficient removal of bubble gas.

After mixing has been completed, vacuum tube 136 is disconnected from fitting 114 and falls away, thereby allowing the pressure within the mixing device to rise to atmospheric pressure. The device is maintained in the sterile field at the time the vacuum tube 136 is removed from fitting 114 so that sterile air flows into the interior of the device and does not contaminate the freshly mixed cement. The end of the tube may fall into a non-sterile field. The cap is then removed from the housing, the cartridge withdrawn, the mixed cement is flowed to the application site, and the prosthetic device is embedded in the cement. These operations are time-critical in order to introduce the cement to the application site at a time when its viscosity is as low as possible.

Vacuum source 110 automatically shuts down the vacuum pump 116 without manual intervention when vacuum tube 136 is removed from fitting 114. The electronic pressure transducer 128 senses the sudden increase of pressure in line 118 resulting from removal of the tube from the fitting and the control circuit then immediately opens switch 123 to deactivate pump 116. Shutdown occurs automatically without a surgeon or attendant having to take the time to search for and actuate a shutdown switch or pedal to deactivate the vacuum pump.

Automatic shutdown of the vacuum source eliminates a variable interval delay in the time critical process of mixing and dispensing bone cement. Cement is delivered to the application site without wasting time to locate and actuate a shutdown switch.

Furthermore, use of the automatic shutdown control eliminates the possibility of people in the operating room shutting down the vacuum pump while the vacuum line is connected to the mixing device. Such premature shutdown of the vacuum pump could result in contamination of the bone cement in the mixing device due to vacuum aspiration of non-sterile material from the non-sterile pump area into the mixing chamber through the vacuum line.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A device for mixing bone cement and removing gas from the cement comprising:
    a) a hollow housing having a wall, an open top and a vacuum tube attachment fitting defining a passage extending through the housing wall;
    b) a bone cement mixing chamber in the housing;
    c) a cap adapted to be fitted on the top of the housing over the mixing chamber to close the housing;
    d) a rotary mixer having a central shaft and a first mixing arm located a distance to one side of the central shaft, said mixing arm extending along the length of the mixing chamber to the bottom of the chamber; and
    e) a mixer drive on the cap, the drive including,
        i) an input drive shaft rotatably mounted on the cap and having an end extending above the cap;
        ii) a rotary drive member attached to the input drive shaft extending above the cap for rotating the input drive shaft;
        iii) an output drive member mounted on the interior of the cap a distance away from the input drive shaft, the output drive member being connected to the rotary mixer central shaft so that rotation of the drive member rotates the central shaft to move the mixer arm in the mixing chamber; and
        iv) drive means joining the input drive shaft and the output drive member for simultaneously moving the output drive member along a closed path extending around the input drive shaft, rotating the output drive member about an axis located away from the input drive shaft, and moving the mixing arm along a first path in the chamber having a number of loops located adjacent to and spaced around the interior sidewall of the chamber and portions extending across the interior of the chamber between successive adjacent loops on the first path.

2. A device as in claim 1 wherein the mixing device drive means includes an interior gear on the cap surrounding the input shaft and a mixer gear attached to the output drive member, said mixer gear being located between said input drive shaft and said interior gear and being meshed with such gear.

3. A device as in claim 2 including a recess formed inside of the cap, said gears being located in the recess.

4. A device as in claim 3 wherein the interior gear extends around the perimeter of the recess.

5. A device as in claim 4 wherein said rotary drive member comprises a hand crank.

6. A device as in claim 2 including a bushing surrounding said output drive member and connection means for mounting the bushing on the inside of the cap.

7. A device as in claim 6 wherein said connection means includes a disk joined to the bushing.

8. A device as in claim 7 including a connection joining the disk to the input drive shaft so that the output drive member is rotated by the input drive shaft.

9. A device as in claim 6 including a drive gear on said input drive shaft, said drive gear engaging said mixer gear.

10. A device as in claim 1 wherein said vacuum tube attachment fitting includes restriction means in said passage for limiting the rate at which gas is vacuum withdrawn from the bone cement mixing chamber to a rate insufficient to entrain particles of dry bone cement with withdrawn gas during initial mixing.

11. A device as in claim 1 wherein said housing includes a bottom wall and a syringe cartridge mounting member on the interior of the bottom wall, and said mixing chamber comprising a syringe cartridge having a cylindrical wall and a piston in the lower end of the cylindrical wall, said syringe cartridge being fitted within said mounting member and having an open top adjacent the top of the housing.

12. A device as in claim 1 wherein said rotary mixer includes a second mixing arm located 180 degrees opposite from said first mixing arm, both said mixing arms extend along the length of the mixer chamber, a cross arm joining the ends of the mixing arms, said mixing arms being spaced apart a distance approximately equal to the interior radius of said syringe cartridge, whereby said drive means moves the second mixing arm along a second path like said first path with the loops of the second path being spaced between the loops of the first path so that said mixing arms are swept through or sufficiently close to the entire volume of the mixing chamber to break bubbles captured within the cement during mixing.

13. A device as in claim 12 including a releasable connection joining the output drive member and the mixer central shaft.

14. A device as in claim 1 wherein said mixer drive means includes an interior gear on the cap surrounding the input drive shaft, a mixer gear attached to the output drive member and meshed with the interior gear, and connection means for moving the output drive member around the input drive shaft.

15. A device as in claim 14 wherein said connection means comprises a member joining the input drive shaft and the output drive shaft.

16. A device as in claim 14 wherein said connection means includes a gear on said shaft meshed with the mixer gear.

17. A device as in claim 1 wherein said vacuum attachment fitting has a wide inlet end at one end of the passageway, a narrow outlet end away from the inlet end and the passageway has a convex wall extending between the ends.

18. A system for mixing bone cement including a device as in claim 1, a vacuum source including a vacuum pump having an inlet port, a vacuum line connecting said vacuum tube attachment fitting and said inlet port, and pump shutdown means for deactivating the pump in response to a sudden increase of pressure at the inlet port.

19. A system as in claim 18 wherein the vacuum source includes an electric pump motor, a power line for the motor, a shutdown switch in the power line and an electronic pressure transducer connected to the inlet port and to the shutdown switch whereby said transducer senses a sudden rise of pressure and opens said switch.

20. A system as in claim 18 including restriction means for limiting initial flow of gas out of the mixing chamber to a rate insufficient to entrain particles of dry bone cement with the withdrawn gas.

21. A device for mixing a volume of bone cement and removing gas from the cement, the device comprising:
 a) a hollow housing having a wall, an open top and a vacuum tube attachment fitting defining a passage through the wall;
 b) a hollow bone cement mixing chamber having an interior sidewall, an open top and a bottom, said mixing chamber located in the housing;
 c) a cap adapted to be fitted on the top of housing to close the housing top and overlie the chamber;
 d) a bone cement mixer in the mixing chamber having a first mixer arm extending from the top of the chamber to a first end located at the bottom of the chamber; and
 e) a mixer drive supported on the cap, said drive including,
  i) an input drive member movably mounted on the cap;
  ii) an output drive member movably mounted on the inside of the cap and located away from the input drive member; said output drive member being connected to said bone cement mixer so that the output drive member and mixer move together;
  iii) a manual drive member outside the cap operatively connected to the input drive member for rotating the input drive member; and
  iv) a second mixer drive member joining the input and output drive members for simultaneously moving the output drive member along a first path within the mixing chamber, rotating the mixer about an axis away from the input drive member and moving the mixer arm along a second path having a plurality of spaced loops located near the chamber sidewall and curved portions which extend through the chamber between successive loops along said second path, when the input drive member is moved by the first mixer drive means.

22. A device as in claim 21 wherein the mixer also includes a second mixer arm like the first arm located in the mixing chamber and spaced from the first mixer arm, and a cross arm joining the lower ends of the first and second arms end near the bottom of the mixing chamber, said second mixer arm movable along a third path like said second path as the output drive member is moved along said first path and the mixer is rotated about said axis so that the first and second mixer arms are swept through or sufficiently close to the entire volume of bone cement in the mixing chamber to break gas bubbles trapped in the bone cement and the third arm is swept over the bottom of the chamber.

23. A device as in claim 22 wherein the cross arm is a rod.

24. A device as in claim 22 wherein the cross arm includes a first mixing blade having a first leading edge and a first deflector extending rearwardly of the first leading edge.

25. A device as in claim 24 wherein the cross arm includes a second mixing blade having a second leading edge and a second deflector extending rearwardly of the second lead edge and wherein each blade has a first side joined to the end of a mixer arm and a second side joined to the second side of the other blade.

26. A device as in claim 25 wherein the first lead edges extends in a first direction and the second lead edge extends in a second direction opposite the first direction.

27. A device as in claim 25 including a piston located in the bottom of the mixing chamber, said piston having a bone cement mixing surface facing the interior of the mixing chamber, wherein the first and second lead edges are located adjacent the bone cement mixing surface so that as the mixer means is rotated, the leading edges scrape an amount of bone cement off the mixing surface and direct the amount of cement upward to mix with the volume of bone cement.

* * * * *

UNITED STATES PATENT AND TRADEMARK OFFICE
CERTIFICATE OF CORRECTION

PATENT NO. : 5,368,386
DATED : NOVEMBER 29, 1994
INVENTOR(S) : WILLIAM M. MURRAY

It is certified that error appears in the above-identified patent and that said Letters Patent is hereby corrected as shown below:

Column 4, line 13, "restriction" should be --restrictions--.

Column 4, line 15, "restrictions" should be --restriction--.

Column 10, line 40, after "to", --the end of-- should be inserted.

Claim 12, column 11, line 32, "1" should be --11--.

Claim 22, column 12, line 60, "end" should be deleted.

Claim 25, column 13, line 12, "lead", should be --leading--.

UNITED STATES PATENT AND TRADEMARK OFFICE
CERTIFICATE OF CORRECTION

PATENT NO. : 5,368,386
DATED : November 29, 1994
INVENTOR(S) : William M. Murray It is certified that error appears in the above-indentified patent and that said Letters Patent is hereby corrected as shown below:

Claim 26, column 14, lines 1 and 2, "lead" should be --leading--.

Signed and Sealed this

Twenty-sixth Day of September, 1995

Attest:

BRUCE LEHMAN

Attesting Officer

Commissioner of Patents and Trademarks